United States Patent [19]

Smolarsky

[11] 4,261,883
[45] Apr. 14, 1981

[54] NOVEL N-ARALKYL ENKEPHALIN AMIDE ANALOGS ARE PROVIDED HAVING ANALGESIC AND OPIOID PROPERTIES

[75] Inventor: Moshe Smolarsky, Rehovot, Israel

[73] Assignee: The Regents of the University of California, Berkeley, Calif.

[21] Appl. No.: 55,563

[22] Filed: Jul. 9, 1979

[51] Int. Cl.$^3$ .................. C07C 103/52; C07C 117/00; A61K 37/00
[52] U.S. Cl. .............................. 260/112.5 R; 260/349; 424/177
[58] Field of Search ................. 424/177; 260/112.5 R, 260/349

[56] References Cited

U.S. PATENT DOCUMENTS 4,127,534  11/1978  Coy et al. .............................. 424/177

FOREIGN PATENT DOCUMENTS 2732451  7/1977  Fed. Rep. of Germany ........... 424/177

*Primary Examiner*—Delbert R. Phillips
*Attorney, Agent, or Firm*—Bertram I. Rowland

[57] ABSTRACT

The enkephalin analogs are polypeptide amides including in the chain the series L-tyrosyl-D-alanyl-glycyl, normally followed by L-phenylalanine. The nitrogen substituents are substituted and unsubstituted phenalkylenes or phenalkenylenes, wherein the alkylenes are of from two to three carbon atoms and the alkenylene of three carbon atoms.

6 Claims, No Drawings

NOVEL N-ARALKYL ENKEPHALIN AMIDE ANALOGS ARE PROVIDED HAVING ANALGESIC AND OPIOID PROPERTIES

The invention described herein was made in the course of, or under, a grant from the National Institutes of Health.

BACKGROUND OF THE INVENTION

1. Field of the Invention

The discovery of the pentapeptide opiate agonists, leu-enkephalin and met-enkephalin offered the opportunity of new analgesics based on amino acids, which might avoid addiction and the other side effects encountered with morphine, its derivatives and synthetic analogs. There has therefore been an intensive effort to develop new low molecular weight polypeptides which would act as opiate agonists without the previously encountered side effects of opiate analgesics, which could be used at low dosages, would not be rapidly degraded in vivo, and would be capable of crossing the blood-brain barrier.

2. Brief Description of the Prior Art

A number of references teach a variety of enkephalin analogs. See for example Hughes, et al., *Nature* 258 577 (1975); Chang, et al. *Life Sciences,* 18, 1473 (1976); and Coy, et al. *Biochem. Biphys. Res. Comm.,* 73, 632 (1976).

SUMMARY OF THE INVENTION

Novel highly active polypeptide agonists are provided which are N-aralkyl or N-aralkenyl substituted enkephalinamide analogs having a polypeptide chain in the amino to the carboxy direction of L-tyrosyl-D-alanylglycyl and normally, L-phenylalnine, with the terminal carboxy as the N-substituted amide. The aralkyl substitution is normally phenalkylene, where the alkylene is of from two to three carbon atoms, and the phenyl may be substituted or unsubstituted.

DESCRIPTION OF THE SPECIFIC EMBODIMENTS

In accordance with the subject invention, novel analgesics or opiate agonists are provided of short chain polypeptides, having at least three members, usually having at least four members, terminating in an N-substituted carboxy amide, wherein the substituent is an aral group of from 0 to 1 site of ethylenic unsaturation i.e. aralkyl and aralkenyl, normally a phenalkylene group, with the alkylene of from two to three carbon atoms, normally polymethylene, and the phenyl group substituted or unsubstituted. The polypeptide chain will include at the carboxy end, going from amine to carboxy, at least the tripeptide group L-tyr-D-ala-gly, and normally the tetrapeptide L-tyr-D-ala-gly-L-phe, where tyr is tyrosine, ala is alanine, gly is glycine and phe is phenylalanine.

For the most part, the compositions of this invention will have the following formula:

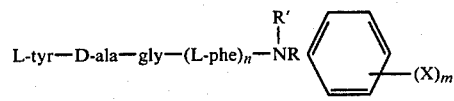

wherein:

R is alkylene of from two to three carbon atoms, preferably polymethylene, or 2-propenylene-1,3;

R' is hydrogen or alkyl of from 1 to 6, usually 1 to 4, more usually 1 to 2 carbon atoms i.e. methyl and ethyl;

X is an electron withdrawing or an electron donating group, usually of from 1 to 20, more usually of from 1 to 12 atoms other than hydrogen, which are carbon, oxygen, nitrogen or sulfur, usually carbon, oxygen and nitrogen, which is substituted on the phenyl, and may be amino, alkylamino or dialkylamino, wherein the alkyl groups are of from one to three carbon atoms; azido, nitro, cyano, halo of atomic number 9 to 53, more usually of atomic number 9 to 35; non-oxo-carbonyl of from 1 to 18, usually 1 to 12, more usually 1 to 4 carbon atoms, including amides and esters, as well as the parent acid; acyl groups of from 1 to 4, usually 1 to 2 carbon atoms; e.g. formyl and acetyl; oxy, including hydroxy and alkoxy of from 1 to 18, usually 1 to 12, more usually 1 to 3 carbon atoms, frequently of from 1 to 2 carbon atoms; thio, including mercapto and alkylthio of the same limitations as alkoxy; alkyl of from 1 to 18, usually 1 to 12, more usually 1 to 3, frequently 1 to 2 carbon atoms; where there is more than one substituent, the substituents may be the same or different;

m is zero to two, usually zero to one; and n is zero to one, usually one.

Of particular interest are the monosubstituted or disubstituted phenyl groups, substituted in either the ortho and/or para position or mixtures thereof. Also preferred are those substituted phenyls which have nitrogen bonded to an annular ring.

The compound can be divided into lipophilic substituted phenyl groups having aliphatic hydrocarbon groups of from 8 to 18, usually 10 to 16 carbon atoms, or weakly lipophilic groups of from 1 to 8, usually 1 to 4 carbon atoms.

The compounds of the subject invention may be prepared in accordance with known techniques. See for example Merrifield, *J. Am. Chem. Soc.* 85, 2149 (1963). Alternatively, employing known protective groups, the polypeptide may be built-up stepwise in solution.

The following examples are offered by way of illustration and not by way of limitation.

EXPERIMENTAL

All temperatures not otherwise indicated are centigrade. All percents and parts not otherwise indicated are by weight, except when mixtures of liquids are employed and are then by volume. The following abbreviations are employed: Z-benzyloxycarbonyl; OBT-O-benzyl tyrosine; TAG-L-tyr-D-ala-gly; TAGP-L-tyr-D-ala-gly-L-phe; DCC-dicyclohexyl carbodiimide; DMF-N,N-dimethyl formamide.

EXAMPLE 1

Synthesis of TAGP

Z-OBT(4 g, $9.86 \times 10^{-3}$ moles) and N-hydroxy succinimide (NHS, 2.3 g, 0.02 moles) were dissolved in 20 ml dioxane-ethyl acetate (1:1) and the solution cooled in an ice-methanol bath ($-10°$ - $-15°$). To the mixture was added DCC (2.1 g, $1.02 \times 10^{-2}$ moles) and the reaction mixture agitated overnight. The temperature was then raised gradually to room temperature, the solids removed by filtration and washed again with ethyl acetate. After evaporation of the solvent, the product was precipitated with isopropanol, filtered and washed again with isopropanol. The ester was then recrystallized from 45 ml isopropanol yielding 3.9 g (79%).

A solution of 1.04 g of the above prepared ester in 10 ml dioxane was mixed with a solution of 0.5 g D-ala-gly ($3.42 \times 10^{-3}$ moles) and 0.55 g potassium bicarbonate ($5.5 \times 10^{-3}$ moles) in 10 ml water. After agitating the mixture overnight at room temperature, 25 ml water, and 25 ml ethyl acetate were added, the mixture cooled in ice and acidified to pH~2 with 2 N sulfuric acid. The product was extracted into the organic phase and the organic phase washed twice with water, once with saturated aqueous brine, dried over sodium sulfate and the solvent then evaporated. The product was precipitated with ethyl ether, filtered and washed with ethyl ether. $R_f=0.6$ ($CHCl_3$-isopropanol-formic acid: 10:1:1).

The formation of the NHS ester with the tripeptide prepared above was repeated. Into 40 ml dioxane-ethyl acetate (1:1) was dissolved the above product (4 g, $7.49 \times 10^{-3}$ moles) and NHS (2.25 g, $1.96 \times 10^{-2}$ moles) and the mixture cooled in an ice-methanol bath and 1.57 g ($7.6 \times 10^{-3}$ moles) of DCC added. After mixing overnight, the temperature was gradually raised to room temperature, followed by filtration, washing the precipitate five times with 10 ml portions of the solvent, the washings combined with the filtrate and the solvent evaporated. The product was then precipitated with isopropanol, filtered and washed with isopropanol, followed by recrystallization from isopropanol. Yield: 2.6 g (55%).

A solution of the above tripeptide ester (4.7 g, $7.45 \times 10^{-3}$ moles) in 50 ml of 1:1 DMF-dioxane was mixed with a solution of phenylalanine (3.7 g, $2.24 \times 10^{-2}$ moles) and potassium bicarbonate, (3 g, $3 \times 10^{-2}$ moles) in 50 ml water. After mixing overnight at room temperature, 200 ml water were added and the mixture cooled in ice and acidified with phosphoric acid to pH 2-3. The product was extracted into the organic phase and DMF-isopropanol 1:1 added to dissolve the precipitate which formed. The organic phase was washed with water, saturated aqueous brine, and dried over sodium sulfate, followed by evaporation and precipitation with diethyl ether, filtration and the solid washed with diethyl ether. $R_f=0.31$ ($CHCl_3$-isopropanolformic acid: 15:1:1).

EXAMPLE 2

Synthesis of o- or p-nitrocinnamyl amine

To a solution of cinnamyl bromide (2 g, $1.02 \times 10^{-2}$ moles) in 10 ml DMF was added 1.88 g ($1.02 \times 10^{-2}$ moles) of potassium phthalimide and the mixture allowed to stand for two hours at room temperature. The mixture was then poured into 250 ml water, the product filtered, washed with water and recrystallized from methanol, yielding 2.5 g (94%).

A solution of potassium nitrate (4.5 g, $4.45 \times 10^{-2}$ moles) in 10 ml sulfuric acid was added dropwise at 25°-30° to a suspension of cinnamyl-gamma-phthalimide (5 g, $1.3 \times 10^{-2}$ moles) in 75 ml acetic acid. The mixture was heated to 68° for one hour, then allowed to cool to room temperature. The mixture was then poured into 250 ml water and ice and 150 ml benzene, the product extracted into the benzene, and the benzene washed with water, aqueous sodium bicarbonate and aqueous saturated brine, followed by drying over sodium sulfate and the solvent then evaporated. The product was recrystallized from ethanol to yield 4.43 g (80%).

The above product (6.6 g, 0.021 moles) was suspended in 50 ml ethanol, followed by the addition of 1.33 ml of anhydrous hydrazine and the mixture refluxed for one hour. After dissolving, a precipitate appeared. The mixture was cooled to room temperature and the solvent evaporated, following by adding 100 ml ethanol and evaporating the ethanol. To the residue was added 100 ml 2 N HCl and the mixture stirred at 50° for 10 min. and then allowed to cool to room temperature for 30 min. Insoluble material was filtered, the precipitate washed with water and to the clear filtrate one volume of ethanol and one volume of n-butanol added, followed by concentrating the mixture to 50 ml. This procedure was repeated three times, the last time evaporating to dryness. The solid residue was treated with diethyl ether, filtered and washed with ether. The o-,p-nitrocinnamylamine appeared as a double spot on TLC, $R_f=0.5, 0.58$ ($CHCl_3$-methanol-formic acid: 10:2:1).

EXAMPLE 3

Synthesis of Z-OBT-D-ala-gly-(p-nitrocinnamylamide)

Z-OBT-D-ala-gly (1 g, $1.87 \times 10^{-3}$ moles) and NHS (0.43 g, $3.74 \times 10^{-3}$ moles) were dissolved in 10 ml of $CH_2Cl_2$-dioxane (1:1) and the solution sooled in an ice-methanol bath ($\sim -10°$) and DCC (0.4 g, $1.94 \times 10^{-3}$ moles) added. After one hour, a solution was added to the reaction mixture, which was prepared as follows: a chilled solution of p-nitrocinnamylamine hydrochloride (1.5 g, $6.93 \times 10^{-3}$ moles) was dissolved in 50 ml water-isopropanol (5:1), which was then extracted into $CH_2Cl_2$-DMF (5:1) under mild basic conditions, dried over sodium sulfate and concentrated to 8 ml. After standing overnight, the reaction mixture was warmed gradually to room temperature, an equal volume of ethyl acetate added, insolubles filtered and washed with ethyl acetate. The ethyl acetate phases were combined, washed with citric acid solution, water, sodium bicarbonate solution, saturated aqueous brine and dried over sodium sulfate, followed by evaporation to approximately 20 ml. A gel-like material appeared to which was added 100 ml of diethyl ether, the mixture filtered and the precipitate washed with ether. The product was recrystalized from water ethanol (1:1) to yield 0.65 g (47%).

EXAMPLE 4

Reduction of the o-, p-nitrocinnamylamides of the peptides to o-, p-aminophenylpropyl amide and formation of azide.

The peptides were hydrogenated with 10% Pd/C in either dioxane (freshly distilled over sodium under nitrogen) or in acetic acid containing 10% water. During the hydrogenation, the protective groups—O-benzyl and N-benzyloxycarbonyl—are removed, the nitro group is reduced to the amino and the double bond is reduced. The procedure employed 20 mg of the peptide and 40-60 mg of 10% Pd/C, mixing the two in 1 ml dioxane and hydrogen gas bubbled through the stirred reaction mixture overnight at room temperature. After filtering of the catalyst, the catalyst was washed with ethanol and the solvent evaporated to dryness by a nitrogen stream.

When the hydrogenation was carried out with the aqueous acetic acid, only 10-20 mg 10% Pd/C per 20 mg of peptide were employed.

The transformation of the amino group to the azide was carried out as follows. The N-aminophenalkylene polypeptide amide prepared above ($2.37 \times 10^{-5}$ moles) was dissolved in 0.2 ml water-0.2 ml ethanol, 30 μl of 2 N HCl added and the solution cooled in ice. To the mixture was added slowly with stirring sodium nitrite (0.22 ml of 0.11 M in water-ethanol, 1:1) and the stirring continued for 20 min. The remaining steps were carried out under red light. To the mixture was added slowly with stirring 0.4 ml of 1 M sodium azide in water-ethanol, 1:1 and the mixture stirred while cooled in an ice bath for two hours. To the reaction mixture was then added 0.8 ml of saturated aqueous brine, 0.8 ml of CHCl$_3$-ethanol (3:1) and 50 μl of 2 N potassium bicarbonate and the product extracted into the organic phase. The extraction was repeated 3× and the combined organic phases dried over sodium sulfate. An equal volume of petroleum ether, 0.8 ml of water-isopropanol (3:1) and 20 microliters 2 N HCl were added and the product extracted into the aqueous phase. The extraction was repeated five times with 0.5 ml portions of water-isopropanol (3:1) containing 0.02 M HCl. After washing the aqueous phase 2× with petroleum ether-chloroform-isopropanol (4:3:1), nitrogen was bubbled through to remove the volatile organic solvents. Ethanol was added to give an ethanol-water 1:1 mixture and the product stored at −20° in the dark.

EXAMPLE 5

Synthesis of Z-OBT-D-ala-gly-L-phe-o-, p-nitrocinnamylamide

Z-OBT-D-ala-gly-L-phe (1.52 g, $2.23 \times 10^{-3}$ moles) and NHS (0.5 g, $4.35 \times 10^{-3}$ moles) were dissolved in a mixture of 5 ml DMF and 10 ml dioxane. After cooling in an ice-ethanol bath (∼−15°), 0.47 g, ($2.29 \times 10^{-3}$ mole) of DCC was added, followed by 30 min. by the addition of a mixture of o-, and p-nitrocinnamylamine as a chilled solution. The solution was prepared from the amine hydrochloride (1.4 g, $6.46 \times 10^{-3}$ moles) by extracting into CH$_2$Cl$_2$ from an aqueous phase under basic conditions (sodium bicarbonate) and then drying over sodium sulfate. The reaction mixture was stirred overnight, warmed gradually to room temperature, insolubles filtered and the precipitate washed with DMF. The product was extracted into ethyl acetate that contained 10% isopropanol, the organic phase washed with aqueous citric acid containing 10% isopropanol, followed by washing with 10% isopropanolic water, 10% isopropanolic aqueous sodium bicarbonate, saturated aqueous brine, and then dried over sodium sulfate.

The same procedure was employed for preparing the mixed o- and p-nitrocinnamylamide of Z-OBT-D-ala-gly, employing 1.32 g, ($2.47 \times 10^{-3}$ moles) of the peptide and 1.5 g ($6.93 \times 10^{-3}$ mole) of the mixed nitrocinnamylamine.

EXAMPLE 6

Synthesis of Z-L-tyr-D-ala-gly-NHCH$_2$CH$_2$C$_6$H$_5$

Into 0.9 ml H$_2$O was suspended 0.33 g D-ala-gly and 315 μl Et$_3$N added. After agitation a solution formed. Into 2 ml DMF was dissolved 0.767 g Z-tyr and 292 μl Et$_3$N added. After cooling the Z-tyr solution to −15° in ice-MeOH, 275 μl isobutyl chloroformate were added, followed by the addition of the D-ala-gly solution after ∼8 min. After stirring for ∼3 hr at −15°, the reaction was continued in the cold room for another 2 days. To the reaction mixture was then added ∼10 ml H$_2$O and the mixture acidified to pH 1-2 followed by ethyl acetate extraction. The organic phase was washed with H$_2$O, saturated brine, dried, (Na$_2$SO$_4$anh) and the solvent evaporated to dryness by flushing with nitrogen. The residue was triturated with ether and then dried in a desiccator to yield 0.51 g of Z-tyr-D-ala-gly.

Into 1 ml DMF was dissolved 0.09 g of the above product, followed by the addition of 28 μl of Et$_3$N and the mixture cooled in an ice-MeOH bath. After adding 29 μl of isobutyl chloroformate and waiting ∼7 min, 65 μl β-phenethylamine were added and the mixture stirred for ∼3 hrs while cooled in the ice-MeOH bath, followed by continuing the reaction overnight in the cold room (4°). To the mixture was then added 10 ml H$_2$O, followed by acidification with HCl to pH ∼1-2 and the product extracted with ethyl acetate. After washing twice with water and repeatedly with aqueous sodium carbonate, the organic phase was washed with saturated brine, dried (Na$_2$SO$_4$) and the solvent evaporated with a nitrogen stream. Addition of a mixture of ether and pet. ether gave 0.0516 g of the desired product.

In order to demonstrate the analgesic activity of the subject invention, in vitro tests were performed which are recognized as demonstrating opiate agonist activity. The first tests performed employed caudate nucleus homogenates. The homogenates were prepared by dissecting four to six caudate nuclei from fresh bovine brains. The organs were washed with buffer C (0.05 M tris-HCl, pH 7.5, sucrose 10%) to remove blood and were homogenized in 240 ml buffer C with a Polytron homogenizer, speed 6, 30 sec. The homogenates were centrifuged at 35 Kxg for 15 min. and the resulting pellets rehomogenated in buffer C and recentrifuged. The pellets obtained (P$_2$) were then homogenized in 240 ml buffer D (0.05 M tris-HCl, pH 7.5) and recentrifuged. The pellets (P$_3$) were homogenized in the required volume of buffer D to obtain a P$_3$ suspension.

For irradiation experiments the P$_3$ pellets were homogenized in 240 ml buffer E (1 mM tris-HCl, pH 7.5), the homogenate centrifuged at 35 Kxg for 10 min and the supernatant collected. This fraction (S$_{4e}$) was a fine suspension and scattered light about ten times less than P$_3$ suspensions. Prior to irradiation, the tris-HCl concentration was raised to 0.05 M, and the particles reaggregated slowly. In the first test, the stereospecific binding affinity of opioids to P$_3$ or S$_{4e}$ fractions were determined by competition with $^3$H-etorphine in the presence of $9 \times 10^{-7}$ M levorphanol or dextrophane. Reaction mixtures were made in 1.5 ml plastic conical centrifugation tubes and contained 1 ml of P$_3$ or S$_{4e}$, 20 microliters of 50 micromolar dextrophane or 20 microliters of 50 micromolar levorphanol and 100 microliters of the competing opioid at various concentrations. After 5 min. at 25°, 20 micromoliters of $7.5 \times 10^{-8}$ M $^3$H-etorphine (30 ci/mmole) were added. The reaction mixtures were stirred at 25° for 20 min. and centrifuged in a Beckman minifuge for 5 min. The supernatant was removed and the bottom of the tube that contained the pellet was cut out and added to a vial containing 10 ml of scintillation liquid (Hanifluor, Mallinckrodt). The vial was vortexed for 10 sec. and the radioactivity counted. For each point, triplets were counted and the average reported. In the second test, the guinea pig ileum test, the ileums were taken from male Hartley guinea pigs, (200-300 g) as described by Freese and Snyder, J. Pharm. Exper. Therapeutics, 194, 205-219 (1975). The test demonstrates the ability of a compound to inhibit voltage induced contractions in the guinea pig ileum. The following table indicates the results obtained in the above tests.

TABLE I

| Compound[a] | $K_d$ in binding to $P_3$ from bovine caudate nucleus homgentate (μM)[c] | I.D.$_{50}$ in the guinea pig ileum test (μM) |
|---|---|---|
| normorphine | 0.09 | .12 |
| (D-ala[2])met-enkephalinamide | — | .012 |
| TAG—NH(CH$_2$)$_2$C$_6$H$_5$ | 0.11 | 0.82 |
| TAG—NH(CH$_2$)$_3$C$_6$H$_4$—p-N$_3$ | 3.8 | 27 |
| TAG—NH(CH$_2$)$_3$C$_6$H$_4$—N$_3$[b] | 1.6 | 5.0 |
| TAGP—NH(CH$_2$)$_3$C$_6$H$_4$N$_3$[b] | 0.038 | 0.028 |
| TAGP—NH(CH$_2$)$_3$C$_6$H$_4$—p-N$_3$ | 0.031 | 0.028 |

[a]TAG—L-tyrosine-D-alanine-glycine
TAGP—L-tyrosine-D-alanine-glycine-L-phenylalanine
[b]A mixture of ortho and para
[c]By competition with $^3$H-etorphine binding to $P_3$.

It is evident from the above results, that the compounds of the subject invention demonstrate substantial analgesic effect in accordance with recognized tests for correlating in vitro analgesic effect with in vivo analgesic effect.

The subject compositions by virtue of their interaction with opiate receptor sites can provide a wide range of physiological effects, such as mood altering effects, analgesia, muscle relaxation, and blood flow regulation.

The subject compounds can also be used for affinity labeling of opiate receptor sites by irradiation of the azido substituted compounds with a mercury lamp under mild conditions. In one experiment, the caudate nuclei homogenate S$_{4e}$ (135 ml) was put in a plastic beaker under nitrogen and 15 ml removed as a control, followed by the addition of either 0.15-0.5 ml 10 mM normorphine hydrochloride or the equivalent volume of water. Stirring the suspension in the dark under nitrogen at 25° for 5 min. and then adding the appropriate azide, stirring for an additional 10 min. in the dark and then irradiating with total light of a mercury lamp (200 watt Osram; lamp housing Oriel Model 6137) at 25° under nitrogen. For each 15 ml sample, 15 ml buffer D were added, the sample centrifuged at 35 Kxg for 40 min., the pellet homogenized in 30 ml buffer D, centrifuded again for 20 min. and the pellets rehomogenized in 7 ml buffer D. Binding activity was assayed with $^3$H-etorphine in 1 ml samples. It was found that normorphine would inhibit the deactivation of the opioid receptors by the azide compounds, but in the absence of the normorphine, total inactivation of the opioid receptors could be achieved.

In employing the subject compounds, the compounds can be administered to a mammalian host in the same manner as other opiate agonists e.g. morphine, are administered. For the most part, the administered dosage will range from about 0.05 to 40 mg, more usually about 0.5 to 20 mg per 70 kg body weight. The drug may be administered neat, admixed with physiologically acceptable powders or dissolved in a physiologically acceptable liquid, e.g. water or aqueous ethanol, usually having not more than about 60 volume percent ethanol. The drug may be administered orally, by inhalation, or parenterally, e.g. subcutaneously, intravenously or intramuscularly. Concentration of the drug and admixtures of solutions will generally range from about 0.5 to 50 weight percent, usually from about one to 30 weight percent. The subject drugs may be used individually or in combination with other drugs, e.g. aspirin or L-dopa.

The subject drugs may be administered as powders, pills, aqueous solutions, tinctures and the like.

The products of this invention also find use as standards in testing for binding to opiate receptor sites for other drugs and investigating the secondary and tertiary structural characteristics of opiate receptor binding sites. Thus, the products can be used in both research and commercial facilities.

In accordance with the subject invention, it is surprisingly found, that the carboxy terminal end of enkephalin can be varied by substituting the 4 and 5th amino acids, particularly the 5th amino acid with an aralkylamino group, either substituted or unsubstituted. The compounds are active analgesics as demonstrated by recognized test procedures.

Although the foregoing invention has been described in some detail by way of illustration and example for purposes of clarity of understanding, it will be obvious that certain changes and modifications may be practiced within the scope of the appended claims.

What is claimed is:

1. A compound of the formula

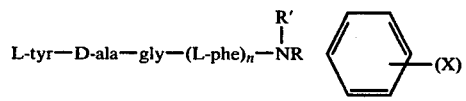

wherein:
R is alkylene of from 2 to 3 carbon atoms or propenylene;
R' is hydrogen or alkyl of from 1 to 2 carbon atoms;
X is a amino, azido or nitro;
n is 0 or 1.

2. A compound according to claim 1, wherein X is amino and n is 1.

3. A compound according to claim 1, wherein X is azido and n is 1.

4. A compound of the formula

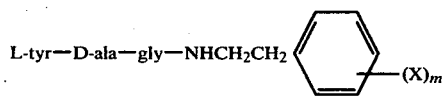

wherein:
X is amino, azido or nitro; and
m is 0 or 1.

5. A compound of the formula

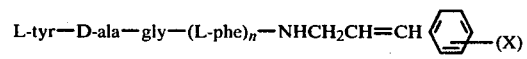

wherein:
X is amino, azido or nitro; and
n is 0 or 1.

6. A compound according to claim 5, wherein X is nitro.

* * * * *